US00PP27567P3

(12) United States Plant Patent
Egger

(10) Patent No.: US PP27,567 P3
(45) Date of Patent: Jan. 17, 2017

(54) HEUCHERA PLANT NAMED 'TNHEUCHA'

(50) Latin Name: ***Heuchera* hybrid**
Varietal Denomination: TNHEUCHA

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 83 days.

(21) Appl. No.: 14/545,499

(22) Filed: May 12, 2015

(65) Prior Publication Data

US 2016/0338252 P1 Nov. 17, 2016

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Upov Pluto Plant Variety Database Sep. 24, 2016 retrieved on Sep. 26, 2016, retrieved from the Internet at <http://www.upov.int/pluto/en/index.jsp> one page.*

* cited by examiner

*Primary Examiner* — June Hwu
(74) *Attorney, Agent, or Firm* — Klarquist Sparkman, LLP; Sheree Rybak

(57) ABSTRACT

A new and distinct *Heuchera* plant characterized by leaves which are multicolored changing from peach to gold to champagne-gold with a strong white veil overall, medium large leaves, light salmon pink flowers on short flowering stems, a medium mounding habit, and excellent vigor.

1 Drawing Sheet

Botanical denomination: *Heuchera* hybrid.
Variety designation: 'TNHEUCHA'.

BACKGROUND OF THE INVENTION

The present invention relates to a new and distinct cultivar of *Heuchera* and given the cultivar name of 'TNHEUCHA'. *Heuchera* is in the family Saxifragaceae. *Heuchera* 'TNHEUCHA' originated as a controlled cross using *Heuchera* 'K760-1', a proprietary, unpatented, unnamed plant as the seed parent, and *Heuchera* 'K626-2', a proprietary, unpatented, unnamed plant as the pollen parent.

Compared to the seed parent, *Heuchera* 'K760-1', the new cultivar is a much larger plant and more free-flowering.

Compared to the pollen parent, *Heuchera* 'K626-2', the new cultivar has larger leaves, is multicolored to gold rather than amber, and is veiled rather than not veiled.

Compared to *Heuchera* 'Ginger Ale', U.S. Plant Pat. No. 18,173, the new cultivar has a larger habit and leaves and more foliage colors.

Compared to *Heuchera* 'Peach Melba', U.S. Plant Pat. No. 17,131, the new cultivar has a larger habit and leaves, greater vigor, and has foliage that turns to gold shades.

This new *Heuchera* is uniquely distinguished by:

1. leaves which are multicolored changing from peach to gold to champagne-gold with a strong white veil overall,
2. medium large leaves,
3. light salmon pink flowers on short flowering stems,
4. a medium mounding habit, and
5. excellent vigor.

This new cultivar has been reproduced only by asexual propagation (tip cuttings and tissue culture). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows eight week old plants of *Heuchera* 'TNHEUCHA' growing in a one gallon container, growing in a cool greenhouse in March in Canby, Oreg.

FIG. 2 shows a one year old plant in flower growing in a one gallon in a cool greenhouse in June in Canby, Oreg.

DETAILED PLANT DESCRIPTION

The following is a detailed description of the new *Heuchera* cultivar based on observations taken in late October of nine-month-old specimens growing in the trail field in full sun in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, $5^{th}$ edition, 2007.

Plant:

*Form*.—Basal rosette, herbaceous perennial.

*Hardiness*.—USDA Zone 4 to 9.

*Size*.—15 cm tall from top of the foliage to the ground and 42 cm wide.

*Number of crowns*.—7.

*Habit*.—Mounding.

*Vigor*.—Excellent.

Leaf:

*Type*.—Simple.

*Arrangement*.—Rosette.

*Shape*.—Broadly ovate to orbicular.

*Number*.—About 70.

*Blade size*.—Grows to 13 cm long and 13.5 cm wide.

*Lobing/division*.—5 to 7 shallow lobes, shallow secondary lobes.

*Venation*.—Palmate.

*Margins*.—Crenate.

*Apex*.—Mucronulate.

*Base*.—Cordate, sometimes overlapping.

*Surface texture*.—Glandular-puberulent on both sides.

*Petiole description*.—Grows to 10 cm long and 2.5 mm wide, glandular hairs, Greyed Red 182B.

*Leaf color*.—Variable, depending on light and temperature; spring topside, from new leaves Red Purple 60A on veins with veil White NN155A and margins Greyed Red 182A to newly mature leaves Greyed Purple 184A on veins with veil White NN155A and margins Greyed Orange 174B to older mature leaves closest to Yellow Green 153A with veins Greyed Purple 184A and veil White NN155A, bottom side closest to 186A; summer topside, Yellow Green 153A with veil NN155A, bottom side Greyed Purple 186A; topside fall has all the top side colors above, bottom side Greyed Purple 186A; winter topside Yellow Green 146A with veil White 155A, bottom side between Greyed Green 195B and Greyed Yellow 160B.

Inflorescence:

*Size*.—Grows to 13 cm wide and 24 cm long.

*Type*.—Semi-upright thyrse.

*Number of flowers per thyrse*.—About 300.

*Flower density*.—Moderate.

*Number of thyrse*.—About 25.

*Peduncle*.—Grows to 24 cm long and 4 mm wide at base, with 0 to 4 petiolate leaves (grow to 5 cm long and 5 cm wide, orbicular to ovate, 5 to 7 lobed, tip apiculate, margins coarsely serrate, base wedge shaped, glandular hairs on both sides, topside Greyed Red 182A to Yellow Green 153A, bottom side 186A) glandular hairs, Greyed Red 178A.

*Pedicel*.—Grows to 3 mm long, with glandular hairs, Greyed Red 178A.

*Bloom period*.—Spring to fall.

Flower bud:

*Size*.—3 mm wide and 5 mm long.

*Description*.—Glandular puberulent, ovoid, down facing.

*Color*.—Red 37C.

Flower:

*Type*.—Perfect.

*Shape*.—Campanulate.

*Attitude*.—Side to down-facing.

*Size*.—6 mm long and 6 mm wide.

*Corolla description*.—5 petals, each 3.5 mm long and 1.3 mm wide, spatulate, margins entire, tip acute, glandular-puberulent and Red 56A on both sides.

*Calyx description*.—Campanulate, 5 mm long and 5 mm wide, with 5 lobes with wide sinuses divided ½ way to the base, each 2 mm wide and 3 mm long, oblong in shape, glandular-puberulent on both sides, tip obtuse, margin entire, Red 36B with lobe tips Yellow Green 153A on both sides and base tinted Green Yellow 1B on outside.

*Stamen description*.—5 in number, filaments 2 mm long, Red 36D, anthers 0.4 mm, Greyed Orange 174A, no pollen.

*Pistil description*.—1, 2-beaked, 4 mm long and 2 mm wide, ovary 2 mm long and 2 mm wide, Green Yellow 1D, style 3 mm long, White NN155A.

*Fragrance*.—None.

*Lastingness*.—Each thyrse blooms for about 3 weeks on the plant.

Fruit and seed: None seed, infertile.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

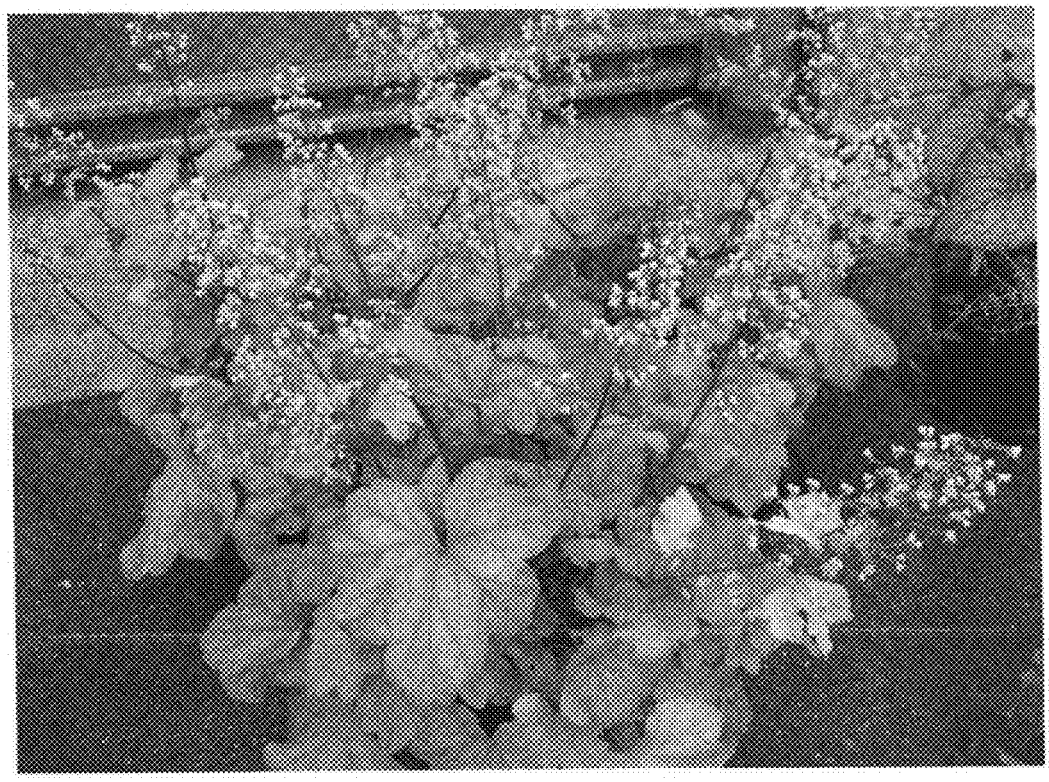

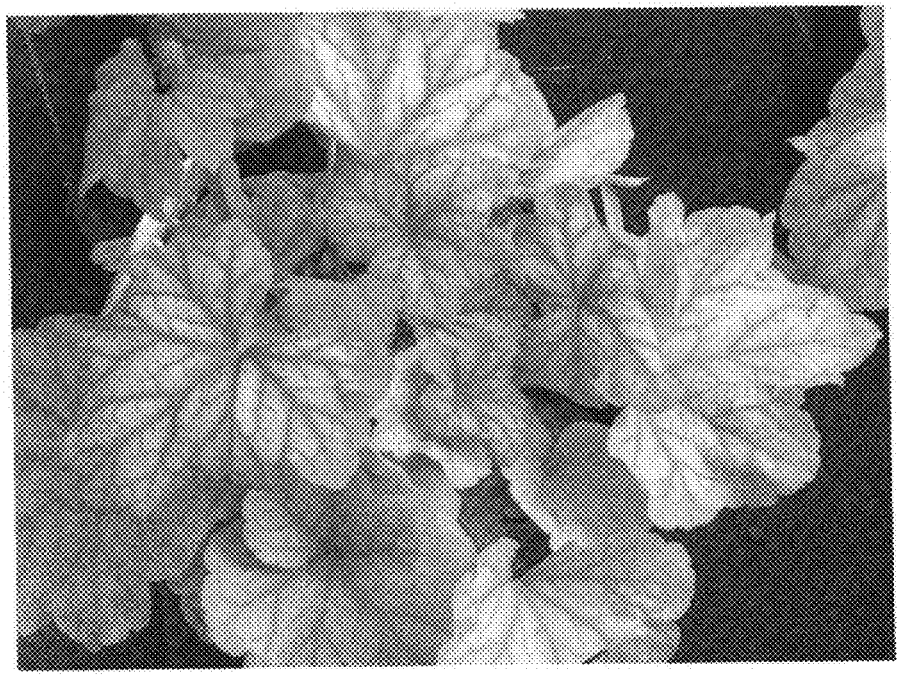
FIG. 1
on left
FIG. 2
below